United States Patent [19]
Miura

[11] Patent Number: 5,282,743
[45] Date of Patent: Feb. 1, 1994

[54] ORTHODONTIC BRACKET

[75] Inventor: Fujio Miura, Tokyo, Japan

[73] Assignee: GAC International, Inc., Central Islip, N.Y.

[21] Appl. No.: 996,551

[22] Filed: Dec. 24, 1992

[51] Int. Cl.⁵ .............................................. A61C 3/00
[52] U.S. Cl. ........................................... 433/8; 433/10
[58] Field of Search ........................... 433/8, 9, 10, 15

[56] References Cited

U.S. PATENT DOCUMENTS

| | | | |
|---|---|---|---|
| 3,946,488 | 3/1976 | Miller et al. | 433/15 X |
| 4,077,126 | 3/1978 | Pletcher | 433/10 |
| 4,597,739 | 7/1985 | Rosenberg | 433/9 X |
| 4,859,179 | 8/1989 | Kesling | 433/8 |
| 5,154,607 | 10/1992 | Hanson | 433/8 |
| 5,160,261 | 11/1992 | Peterson | 433/10 X |
| 5,161,969 | 10/1992 | Pospisil | 433/8 |

FOREIGN PATENT DOCUMENTS

| | | | |
|---|---|---|---|
| 444754 | 3/1936 | United Kingdom | 433/10 |
| 9107925 | 6/1991 | World Int. Prop. O. | 433/10 |

*Primary Examiner*—Gene Mancene
*Assistant Examiner*—Thomas Price
*Attorney, Agent, or Firm*—Kenyon & Kenyon

[57] ABSTRACT

An orthodontic bracket is provided for use with an arch wire. The bracket includes a bracket main member having upper, middle and lower portions. The middle portion includes a slot formed therein for receiving the arch wire. Wings are formed on the upper and lower portions of the bracket main member for enabling a ligature to be tied therewith to secure the arch wire in place in the slot. Engaging portions are formed on the wings for enabling the ligature to be held in a tied state on the wings such that the ligature avoids pressured contact with the arch wire, thereby allowing the bracket to move smoothly along the arch wire during orthodontic treatment requiring such movement.

14 Claims, 7 Drawing Sheets

ORTHODONTIC BRACKET

FIELD OF THE INVENTION

This invention relates generally to orthodontic brackets used with arch wires in orthodontic treatment.

BACKGROUND INFORMATION

Orthodontic brackets may be used with arch wires in orthodontic treatment for straightening teeth. The brackets, which are attached to the surfaces of the teeth, typically include a main member portion with a generally U-shaped slot formed in the center therein for holding the arch wire. A pair of wings are formed integrally in the upper and lower portions of the bracket main member, enabling ligature means to be tied to the bracket to retain the arch wire in the slot. Tensile and bending forces from the arch wire can thereby be applied to the tooth.

During orthodontic treatment, the brackets are first attached to tooth surfaces using adhesives. The arch wire is then positioned within the slots in each bracket main member, and ligature means are tied to the wings to retain the arch wire in the slots. Stainless ligature wire or elastomeric ligature rings are conventionally used as the ligature means.

The arch wire is generally firmly tied to the brackets. However, when prescribed shifting of teeth is required during orthodontic treatment, the brackets attached to the teeth must be capable of shifting or moving along the arch wire as the teeth shift. Proper tooth shifting is difficult unless the brackets can move smoothly along the arch wire.

Moreover, it is now possible to apply weak continuous loads to the teeth using superelastic arch wires. It is, therefore, important that brackets be able to move along the arch wire without excessive friction therebetween.

When stainless steel ligature wire is used as the ligature means with prior art brackets, the arch wire is firmly tied to the bracket as the ligature wire is in contact with the underside of the wings and with the arch wire under strong pressure. The arch wire thereby becomes firmly attached to the bracket. As a result, shifting the bracket smoothly along the arch wire is difficult because of friction between the arch wire and the bracket.

If ligature wire is to be used in orthodontic treatment that requires the bracket to shift along the arch wire, it is necessary to form a gap between the ligature wire and the arch wire by positioning the ligature wire away from the arch wire. This type of ligature work is, however, difficult.

Elastomeric ligature rings may also be used as the ligature means to secure the arch wire within the slot. Use of elastomeric ligature rings is relatively simple because of the elasticity of the rings. However, even with elastomeric ligature rings, the arch wire becomes firmly attached to the bracket main member because a portion of the ligature ring will be under strong elastic pressure against the arch wire. As a result, it is difficult to shift the bracket smoothly along the arch wire.

Figure 9:
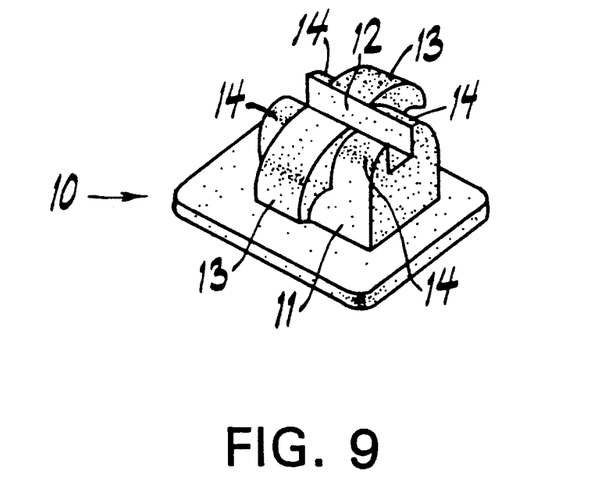
FIG. 9 is a perspective view of an improved prior bracket developed by the inventor.

In an attempt to solve the problems with prior art brackets, an improved bracket 10 shown in FIG. 9 was described in Japanese Patent Public Disclosure Hei 3-21236. The bracket 10 includes a bracket main member 11 having a U-shaped slot 12 formed in a central portion therein for holding an arch wire (not shown). A pair of wings 13 for retaining ligature means (not shown) are formed on the upper and lower portions of bracket main member 11. The bracket 10 differs from prior brackets in that shoulder portions 14 for supporting the ligature means are integrally formed outside the slot 12 on both sides of bracket main member 11.

With the improved bracket 10, regardless of whether stainless steel ligature wire or elastomeric ligature rings are used as the ligature means, the arch wire is tied to the bracket so that a gap is formed beneath the ligature means and the arch wire. The ligature means is supported on the upper surfaces of shoulder portions 14 on both sides of bracket main member 1, thereby enabling the gap to be formed between the ligature means and the arch wire. As a result, there is no pressured contact between the ligature means and the arch wire. Consequently, as the tooth shifts during orthodontic treatment, the bracket attached to the tooth surface can shift smoothly along the arch wire.

The shoulder portions 14 of the bracket are integrally connected to the sides of bracket main member 11, enlarging the width of the bracket 10 at the two shoulder portions 14. Small brackets are, however, preferred for orthodontic treatment. The presence of the shoulder portions 14 increases the difficulty of pushing the arch wire inside the slot 12. This problem is particularly apparent when using the brackets on the front row of teeth in the lower jaw where distances between brackets are small. Also, the process of forming the shoulder portions 14 on the bracket 10 is difficult and expensive.

The presence of shoulder portions 14 makes it possible to reduce pressured contact between the ligature means and the arch wire, which is desirable for cases in which the bracket 11 should shift along the arch wire. However, for orthodontic treatment requiring the bracket 10 to be firmly tied to the arch wire, the presence of the shoulder portions 14 makes firm attachment of the arch wire and bracket main member 11 difficult.

SUMMARY OF THE INVENTION

Brackets in accordance with the present invention include a bracket main member having a slot formed in the central portion thereof for receiving an arch wire. Wings are formed in the upper and lower portions of the bracket main member to enable ligature means to be tied thereon to retain the arch wire inside the slot. The wings include engaging portions to retain the ligature means on the wings in a tied state. The engaging portions may comprise indentations or projections.

To use brackets according to the present invention for treatment requiring the bracket main member to shift along the arch wire, the ligature means is tied on the bracket engaging the engaging portions of each wing. In this tied state, the ligature means is positioned such that it avoids pressured contact with the arch wire. Thus, when a tooth shifts during orthodontic treatment, the bracket main member attached to the tooth surface is able to shift smoothly along the arch wire.

For orthodontic treatment requiring a firm attachment of the bracket main member and the arch wire, the ligature means is tied on the wings of the bracket without utilizing the engaging portions. A portion of the ligature means is thereby positioned on both sides of the bracket main member so that there is a direct pressured contact between the ligature means and the arch wire, making it possible to attach the arch wire firmly to the bracket main member.

DETAILED DESCRIPTION

Figure 1:
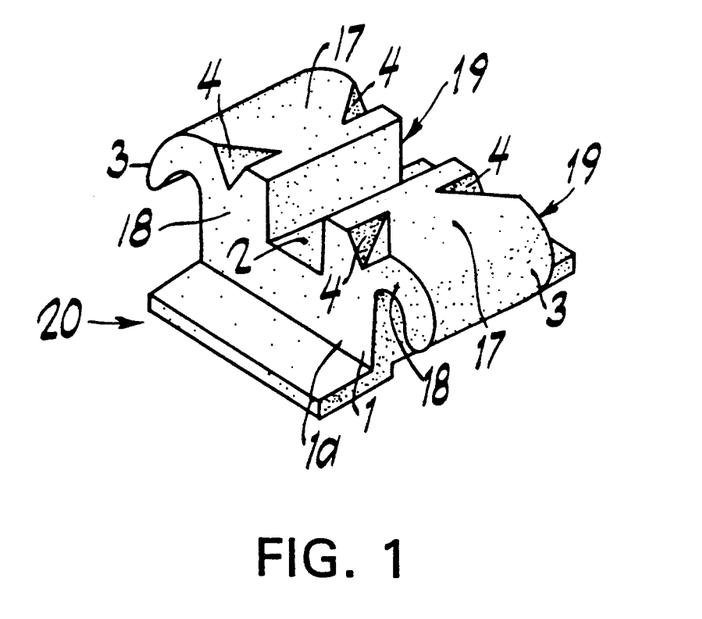
FIG. 1 is a perspective view of an orthodontic bracket in accordance with one embodiment of the present invention.

FIG. 1 illustrates a single wing type bracket 20 constructed in accordance with one embodiment of the present invention. The bracket 20 is similar to the improved bracket 10 shown in FIG. 9, in that, a U-shaped slot 2 for maintaining an arch wire within the bracket is formed in a central portion of the bracket main member 1. A pair of tie-wings or wings 3 for retaining ligature means (not shown) are formed in the upper and lower portions of bracket main member 1. The tie wings 3 each include a buccal surface 17, a mesial surface 18 and a distal surface 19. What distinguishes the bracket 20 are the hitching or engaging portions 4 comprising V-shaped or U-shaped indentations formed at the intersection of the buccal surface 17 and one of the mesial and distal surfaces 18 and 19 on both side surfaces of each wing 3 that are capable of retaining the ligature means.

The engaging portion indentations 4 enable the ligature means to be tied and positioned such that the ligature means avoid direct contact with the arch wire. The indentations 4 should be sufficiently deep to retain the arch wire and should be formed at prescribed distances from the edges of slot 2.

Figure 2A:
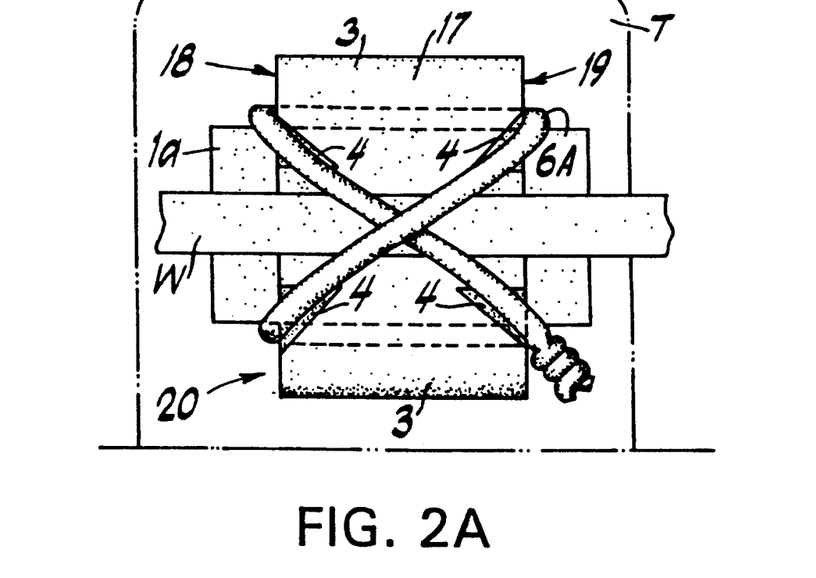
FIG. 2A is a front elevational view of the bracket shown in FIG. 1 with a ligature installed thereon.
Figure 2B:
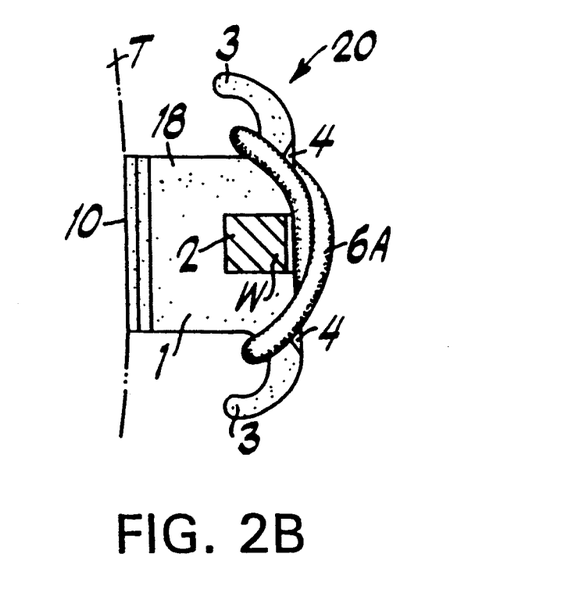
FIG. 2B is a side elevational view of the bracket shown in FIG. 2A.

Brackets 20 in accordance with the invention may be used in orthodontic treatment to straighten a patient's teeth by first affixing the brackets to the teeth. As shown in FIGS. 2A and 2B, the bottom surfaces of the bottom portions 1a of the bracket main members 1 are affixed to the surface of teeth T with adhesives as with prior art brackets. The arch wire W is then placed inside the slot 2 of each bracket 20. The arch wire W is secured within the slot 2 by tying ligature means 6A to the wings 3, thereby enabling the arch wire W to apply forces to the teeth T during treatment. This ligature means 6A shown in FIGS. 2A and 2B comprise a ligature wire.

Four indentations 4 are formed on the wings 3 of the bracket 20. The indentations 4 are formed on both sides of each wing 3 at the intersection of the buccal surface 17 and one of the mesial and distal surfaces 18 and 19. For orthodontic treatment requiring the bracket 20 to shift along arch wire W, the ligature wire 6A is twisted and hitched within the indentations 4 of each wing 3 as shown in FIG. 2A to tie the arch wire W to bracket main member 1. As shown in FIG. 2B, the ligature wire 6A is positioned on the outer surface of each wing 3 so that it does not exert pressure against the arch wire W. Thus, when the tooth T moves during orthodontic treatment, the bracket main member 1 attached to the surface of the tooth T shifts smoothly along arch wire W. Although a ligature wire 6A is used as the ligature means in the drawings, elastomeric ligature rings may also be used in a similar manner.

Figure 3A:
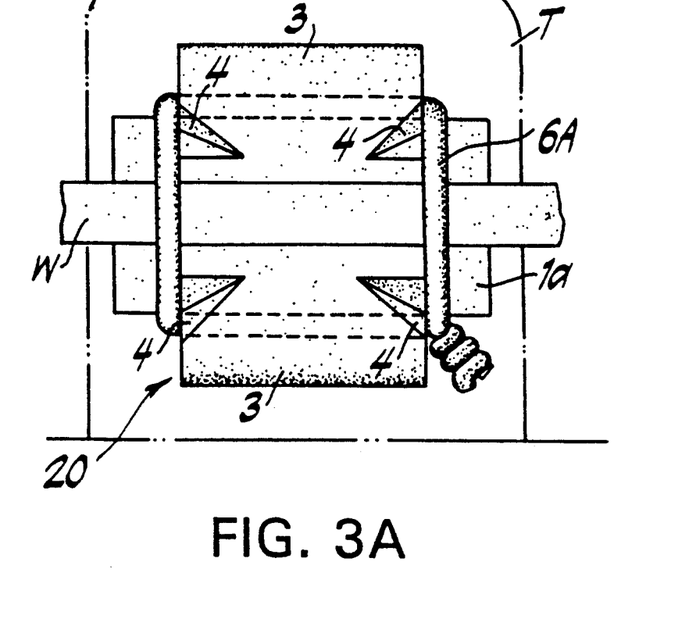
FIG. 3A is a front elevational view of the bracket shown in FIG. 1 with a ligature installed thereon in an alternate manner.
Figure 3B:
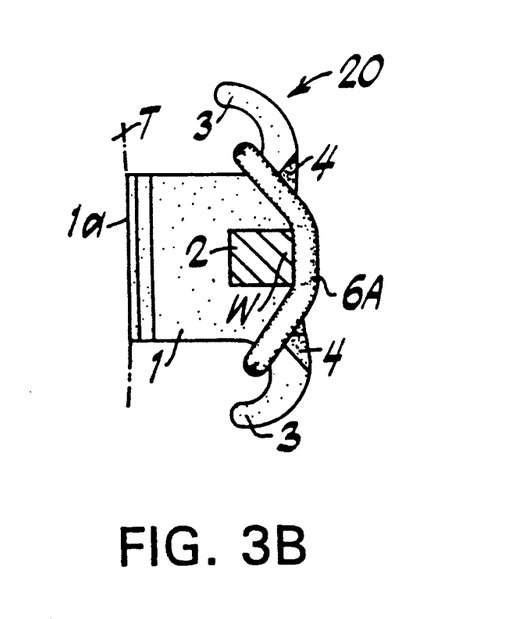
FIG. 3B is a side elevational view of the bracket shown in FIG. 3A.

Alternately, for treatment that requires the bracket main member 1 and arch wire W to be firmly fastened, the ligature wire 6A may be tied to the wings 3 without using the indentations 4 as shown in FIGS. 3A and 3B. As shown in FIG. 3B, a portion of ligature wire 6A is positioned on both sides of bracket main member 1 so that there is direct pressured contact between arch wire W and the ligature wire 6A. The arch wire W can thereby be firmly attached to the bracket main member 1. Thus, a simple change in the manner in which the ligature 6A is tied makes the bracket 20 effective for use in treatment requiring firm fastening of the bracket main member 1 to arch wire W.

Figure 4:
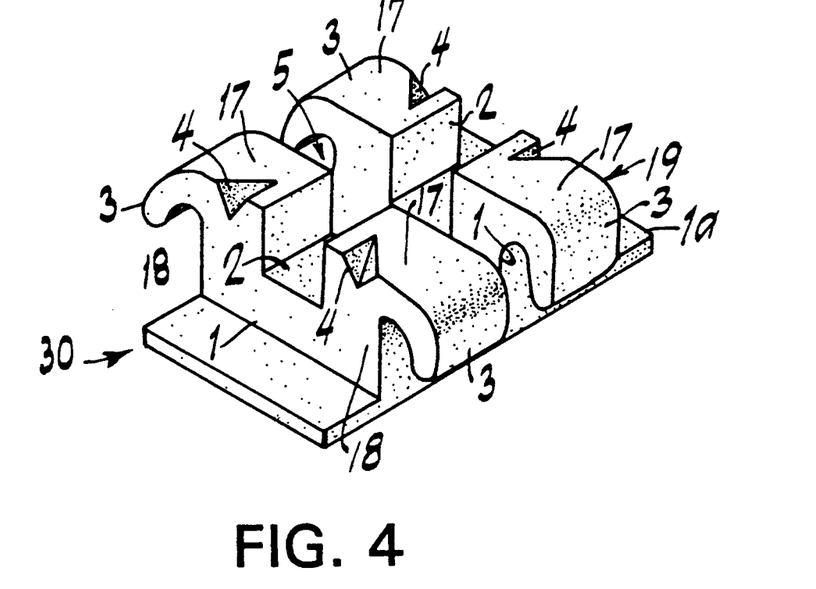
FIG. 4 is a perspective view of an orthodontic bracket in accordance with another embodiment of the invention.

A second example of a bracket in accordance with the invention is a twin type bracket 30 shown in FIG. 4. The bracket 30 includes a main member 1 with wings 3 extending therefrom, which are separated by a partition slot 5. Four indentations 4 are formed at the outer edges of the wings 3 at the intersection of the buccal surface 17 and one of the mesial and distal surfaces 18 and 19 of the wings 3 in a manner similar to the bracket 20 of the first embodiment.

Figure 5:
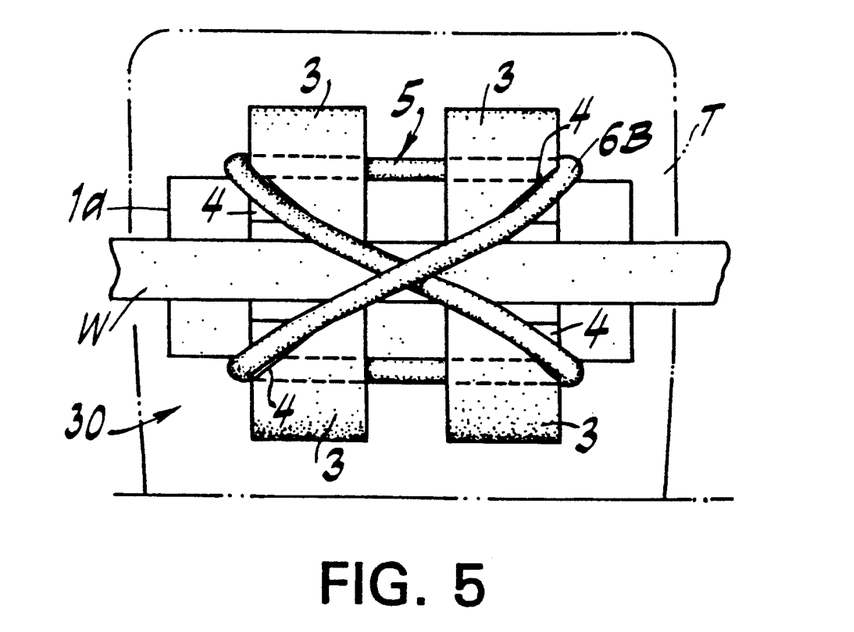
FIG. 5 is a front elevational view of the bracket shown in FIG. 4 with a ligature installed thereon.

To use a bracket 30 in treatment requiring the bracket main member 1 to shift along arch wire W, an elastomeric ligature ring 6B may be installed on the bracket 30 utilizing the indentations 4 as shown in FIG. 5. The ligature ring 6B thereby avoids pressured contact with arch wire W in a manner similar to the ligature means used with the bracket 20. Thus, when tooth T shifts during treatment, the bracket main member 1 attached to the surface of the tooth T is able to shift smoothly along arch wire 1.

Figure 6:
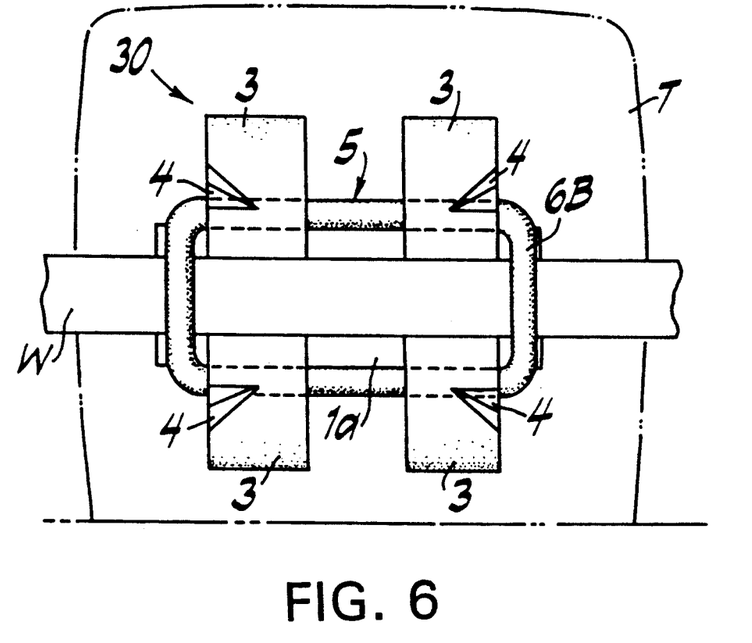
FIG. 6 is a front elevational view of the bracket shown in FIG. 4 with a ligature installed thereon in an alternate manner.

For treatment requiring a firm attachment between bracket main member 1 and arch wire W, the ligature ring 6B is tied to the bracket using the wings 3 without using the indentations 4 as shown in FIG. 6. With this arrangement, a portion of ligature ring 6B is in direct pressured contact with arch wire W, enabling the arch wire W to be firmly attached to the bracket main member 1.

It should be noted that although an elastomeric ligature ring 6B is used as the ligature means in the example illustrated above, similar results could be obtained if ligature wire 6A were used as was shown with the bracket 20 in FIGS. 2A, 2B, 3A and 3B.

Figure 7:
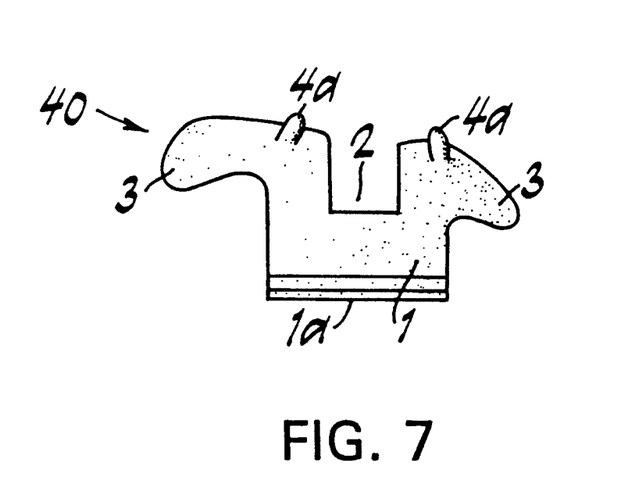
FIG. 7 is a side elevational view of an orthodontic bracket in accordance with another embodiment of the present invention.
Figure 7A:
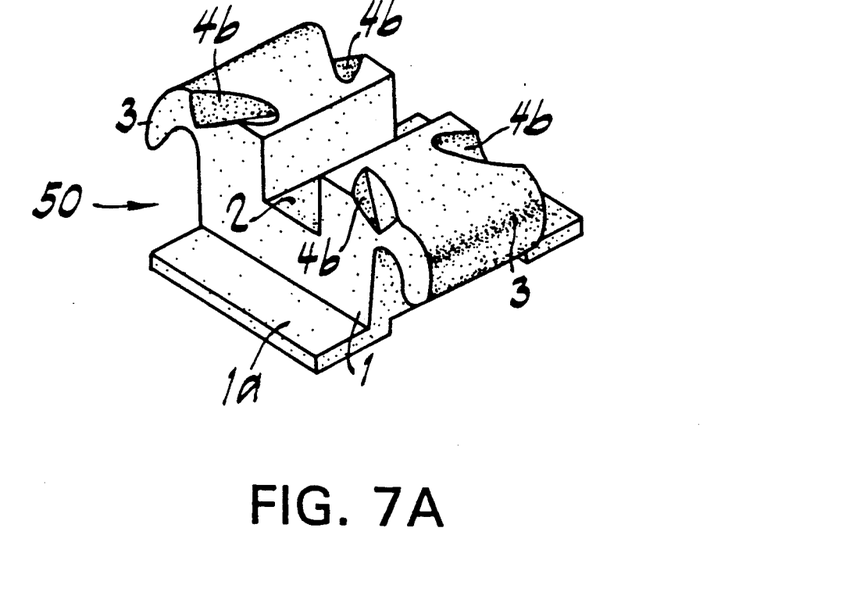
FIG. 7A is a perspective view of an orthodontic bracket in accordance with another embodiment of the invention.
Figure 7B:
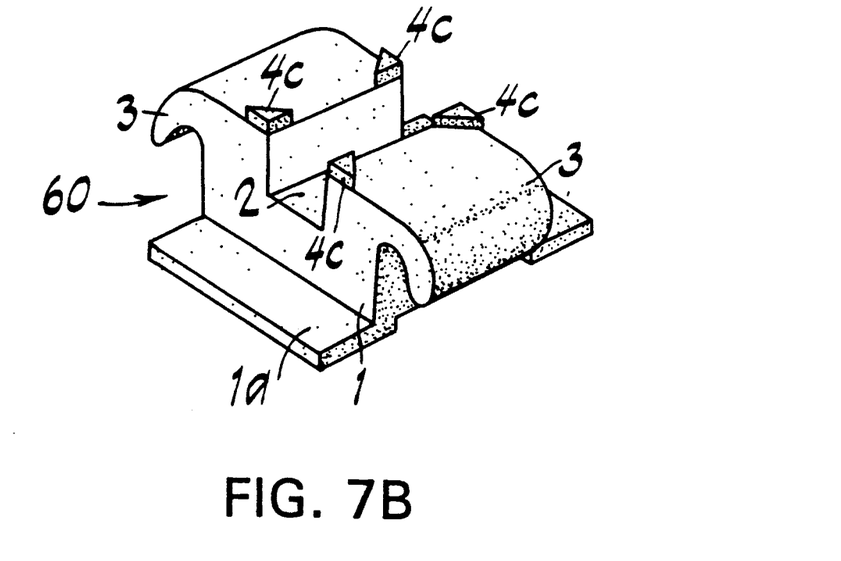
FIG. 7B is a perspective view of an orthodontic bracket in accordance with another embodiment of the invention.

Although the engaging portions for the ligature means shown in the previously described brackets 20 and 30 comprised indentations 4, other means for securing the ligature means may also be used like, for example, the projections 4a on the bracket 40 as shown in FIG. 7 and the projections 4c on the bracket 60 shown in FIG. 7B. The projections 4a can be formed on the upper surfaces of wings 3 and can also be formed connected or integral with the side surfaces of wings 3. They can be positioned centripetally or centrifugally on the bracket main member 1. The projections 4c shown in FIG. 7B may also be formed centripetally or centrifugally on the bracket main member 1.

Figure 8:
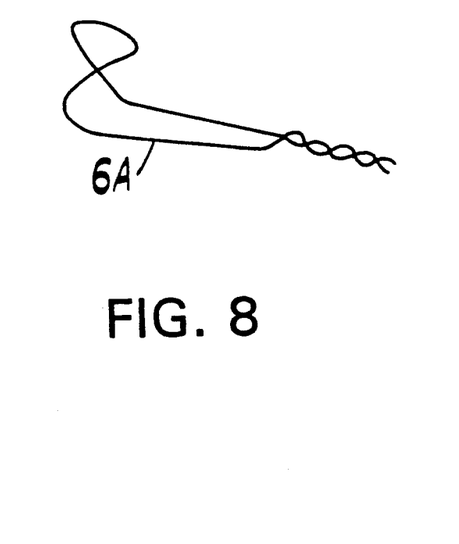
FIG. 8 is a perspective view of a ligature wire.

With regard to the use of the ligature wire 6A in a tied state, it may be convenient to have an "X" shape suitable for tying previously imparted on the wire as shown in FIG. 8. Use of such an X-shaped ligature wire 6A with brackets in accordance with the invention is preferred.

The present invention enables bracket main members to shift smoothly along the arch wire during treatment requiring such movement. The invention also makes it possible to attach the arch wire firmly to the bracket main member for treatment requiring a firm attachment of the arch wire and the bracket.

Brackets in accordance with the present invention differ from the prior improved bracket 10 shown in FIG. 9 in that engaging portions are formed in the wings of the brackets, eliminating the need to enlarge the width of the bracket. Engaging portions comprising indentations are easy to form on the brackets.

Also, because brackets in accordance with the invention can be made small, arch wires can be easily positioned in the slots of each bracket main member. This is particularly advantageous where distances between brackets are small as when placed on the front row of teeth in the lower jaw.

Although the present invention has been described with respect to specific embodiments thereof, various changes and modifications may be suggested to one skilled in the art. Such changes and modifications are encompassed in the invention as fall within the scope of the appended claims.

I claim:

1. An orthodontic bracket for use with an arch wire, comprising:
   a bracket main member having upper, middle and lower portions, the middle portion having a slot formed therein for receiving the arch wire;
   wings formed on the upper and lower portions of the bracket main member for enabling a ligature means to be tied therewith in a tied state to secure the arch wire in place in the slot, said wings including a buccal surface and mesial and distal surfaces; and
   ligature engaging portions formed on the wings at the intersection of said buccal surface and one of said metal and distal surfaces for enabling the ligature means to be held in place in the tied state on the wings and avoiding pressured contact between the ligature means and the arch wire.

2. The orthodontic bracket of claim 1, wherein the engaging portions comprise indentations.

3. An orthodontic bracket for use with an arch wire, comprising:
   a bracket main member having upper, middle and lower portions, the middle portion having a slot formed therein for receiving the arch wire;
   wings formed on the upper and lower portions of the bracket main member for enabling a ligature means to be tied therewith to secure the arch wire within the slot, said wings including a buccal surface and mesial and distal surfaces; and
   ligature engaging portions formed on the wings at the intersection of said buccal surface and one of said metal and distal surfaces, the engaging portions being adapted to retain the ligature means in a tied position on the wings such that the ligature means avoids pressured contact with the arch wire.

4. The orthodontic bracket of claim 3, wherein the engaging portions comprise indentations.

5. The orthodontic bracket of claim 3, wherein the orthodontic bracket comprises a twin type bracket.

6. The orthodontic bracket of claim 3, wherein the orthodontic bracket comprises a single wing type bracket.

7. An orthodontic bracket comprising:
   a bracket main member having a slot formed therein for receiving an arch wire;
   wings extending from said bracket main member on opposite sides of said slot to enable a ligature means to be coupled with the wings in a tied state to retain the arch wire in said slot, said wings including a buccal surface and mesial and distal surfaces; and
   ligature engaging means on said wings at the intersection of said buccal surface and one of said mesial and distal surfaces adapted to engage the ligature means such that the ligature means is maintained in the tied state on said wings with the ligature means avoiding pressured contact with the arch wire.

8. The orthodontic bracket of claim 7, wherein said engaging means comprise indentations.

9. The orthodontic bracket of claim 7, wherein the orthodontic bracket comprises a twin type bracket.

10. The orthodontic bracket of claim 7, wherein the orthodontic bracket comprises a single type bracket.

11. A orthodontic bracket comprising:
    a bracket main member having a slot formed therein for receiving an arch wire;
    a pair of wings extending from said bracket main member on opposite sides of said slot to enable a ligature means to be coupled with the wings in a tied state to retain the arch wire in said slot, said wings including a buccal surface and mesial and distal surfaces; and
    ligature engaging means formed on said wings at the intersection of said buccal surface and one of said mesial and distal surfaces, said engaging means being engageable with the ligature means to maintain the ligature means in the tied state on said wings such that contact between the ligature means and the arch wire is inhibited.

12. The orthodontic bracket of claim 11, wherein said engaging means comprise indentations.

13. An orthodontic bracket for use with an arch wire, comprising:
    a bracket main member having upper, middle and lower portions, the middle portion having a slot formed therein for receiving the arch wire, the bracket main member including a buccal surface and mesial and distal surfaces;
    wings formed on the upper and lower portions of the bracket main member for enabling a ligature means to be tied therewith to secure the arch wire within the slot; and ligature engaging portions formed on the bracket main member at the intersection of said buccal surface and one of said mesial and distal surfaces, the engaging portions being adapted to retain the ligature means in a tied position on the wings such that the ligature means avoids pressured contact with the arch wire.

14. The orthodontic bracket of claim 13, wherein the engaging portions comprise indentations.

* * * * *

UNITED STATES PATENT AND TRADEMARK OFFICE
CERTIFICATE OF CORRECTION

PATENT NO. : 5,282,743
DATED : February 1, 1994
INVENTOR(S) : Fujio MIURA

It is certified that error appears in the above-indentified patent and that said Letters Patent is hereby corrected as shown below:

Column 2, line 32, delete the comma on that line.

Column 2, line 33, close up to continue after line 31.

Column 6, line 8, change "metal" to --mesial--.

Column 6, line 19, after "bracket" insert a comma.

Signed and Sealed this

Eighteenth Day of October, 1994

Attest:

BRUCE LEHMAN

*Attesting Officer*     *Commissioner of Patents and Trademarks*